(12) United States Patent
Klever et al.

(10) Patent No.: US 11,564,726 B2
(45) Date of Patent: Jan. 31, 2023

(54) DISPENSING SYSTEM FOR USE IN CRYOGENIC SKIN TREATMENT

(71) Applicant: Dutch Renewable Energy B. V., Muiden (NL)

(72) Inventors: Diede Hendrik Paul Klever, Amsterdam (NL); Hubert Clemens Pellikaan, Utrecht (NL)

(73) Assignee: Dutch Renewable Energy B.V, Muiden (NL)

( * ) Notice: Subject to any disclaimer, the term of this patent is extended or adjusted under 35 U.S.C. 154(b) by 382 days.

(21) Appl. No.: 16/744,866

(22) Filed: Jan. 16, 2020

(65) Prior Publication Data

US 2020/0146739 A1 May 14, 2020

Related U.S. Application Data

(63) Continuation of application No. PCT/EP2018/069167, filed on Jul. 13, 2018.

(30) Foreign Application Priority Data

Jul. 19, 2017 (EP) ..................................... 17182068

(51) Int. Cl.
*A61B 18/02* (2006.01)
*B65D 83/28* (2006.01)
*A61M 11/02* (2006.01)
*C07C 43/04* (2006.01)

(52) U.S. Cl.
CPC ......... *A61B 18/0218* (2013.01); *A61M 11/02* (2013.01); *B65D 83/285* (2013.01); *C07C 43/043* (2013.01)

(58) Field of Classification Search
CPC ..................................................... A61B 18/02
See application file for complete search history.

(56) References Cited

U.S. PATENT DOCUMENTS

| 4,417,674 | A |   | 11/1983 | Giuffredi |              |
|-----------|---|---|---------|-----------|--------------|
| 4,549,243 | A | * | 10/1985 | Owen      | B05B 5/0255  |
|           |   |   |         |           | 346/143      |
| 4,949,764 | A | * | 8/1990  | Clusserath| B67C 3/286   |
|           |   |   |         |           | 141/39       |
| 5,125,546 | A |   | 6/1992  | Dunne et al. |           |
| 5,516,505 | A |   | 5/1996  | McDow     |              |

(Continued)

FOREIGN PATENT DOCUMENTS

| SU | 419236 A * | 8/1974 |
| WO | WO-2016/010428 | 1/2016 |

OTHER PUBLICATIONS

International Search Report and Written Opinion for International Application No. PCT/EP2018/069167, dated Nov. 6, 2018, 11 pages.

*Primary Examiner* — Joanne M Hoffman
*Assistant Examiner* — Nora W Rhodes
(74) *Attorney, Agent, or Firm* — Foley & Lardner LLP

(57) ABSTRACT

The invention relates to a dispensing system for use in cryogenic skin treatment that is capable of targeted delivery of a cryogen at a high rate, thereby achieving rapid freezing of targeted skin tissue. The dispensing system of the present invention uses a cryogen that contains dimethyl ether and is designed to deliver the cryogen in an accurate and very effective manner.

15 Claims, 8 Drawing Sheets

(56) References Cited

U.S. PATENT DOCUMENTS

Figure 1A:
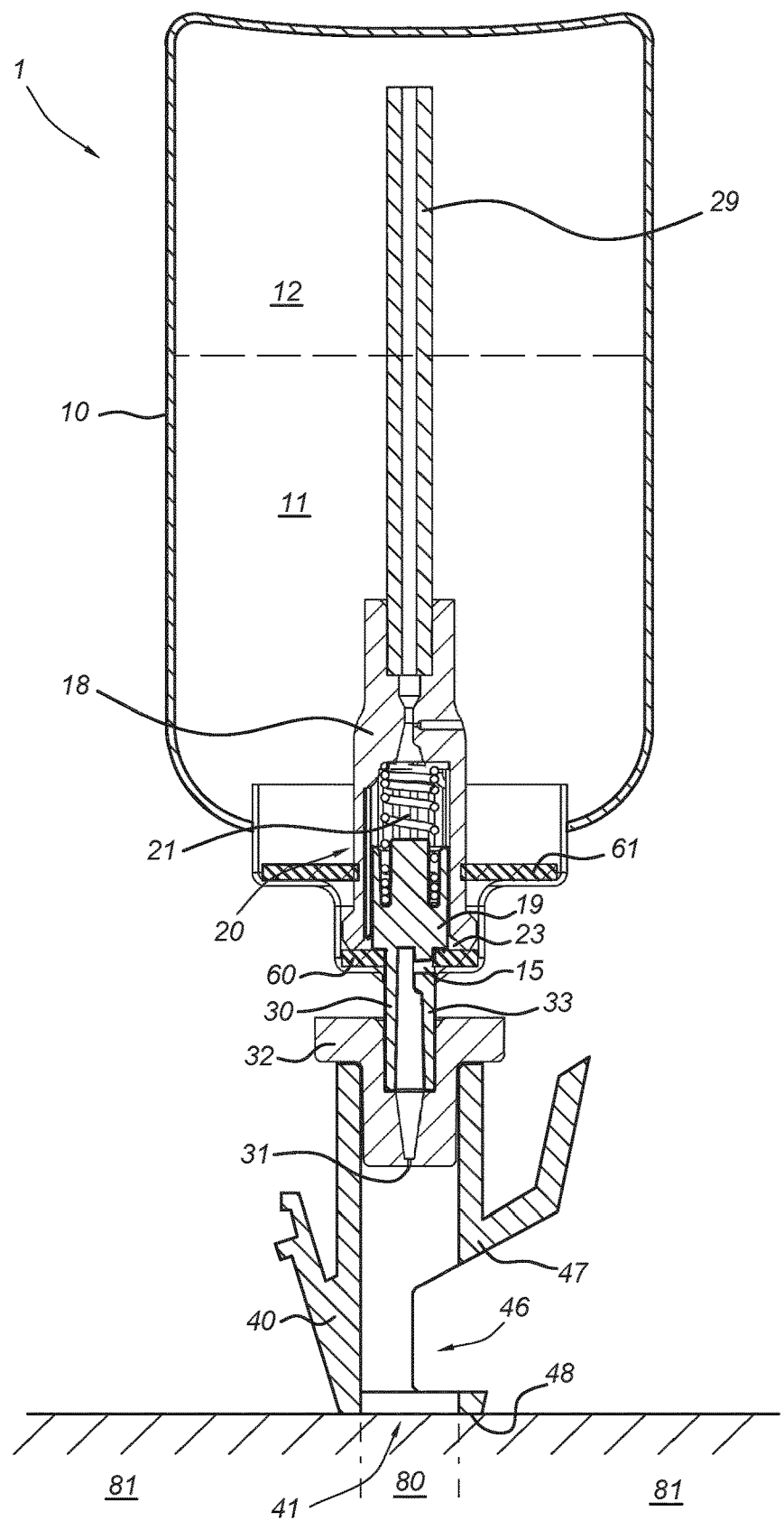

| | | | |
|---|---|---|---|
| 5,570,819 A * | 11/1996 | Uehira | B05B 11/306 |
| | | | 222/255 |
| 2004/0102768 A1 | 5/2004 | Cluzeau et al. | |
| 2005/0043723 A1 * | 2/2005 | Howlett | A61B 18/0218 |
| | | | 606/26 |
| 2007/0054018 A1 * | 3/2007 | Yuan | C11B 5/00 |
| | | | 426/417 |
| 2007/0056585 A1 * | 3/2007 | Davies | B05B 11/3056 |
| | | | 128/203.15 |
| 2014/0048617 A1 * | 2/2014 | Furner | B65D 83/285 |
| | | | 239/55 |
| 2015/0352577 A1 * | 12/2015 | Burrowes | B05B 11/3084 |
| | | | 239/304 |
| 2017/0189627 A1 * | 7/2017 | Klever | A61M 19/00 |

\* cited by examiner

DISPENSING SYSTEM FOR USE IN CRYOGENIC SKIN TREATMENT

CROSS-REFERENCE TO RELATED APPLICATIONS

This application is a continuation of International Application No. PCT/EP2018/069167, filed on Jul. 13, 2018, which claims the benefit of and priority to European Application No. 17182068.1, filed on Jul. 19, 2017, both of which are hereby incorporated by reference herein in their entireties.

TECHNICAL FIELD OF THE INVENTION

The present invention relates to a dispensing system for use in cryogenic skin treatment. The dispensing system of the present invention comprises:
- a container comprising a cryogen;
- an actuatable valve comprising a chamber and a nozzle connected to the outlet of said chamber;
- a spacer attached to the container or the valve, said spacer being adapted for defining a predetermined distance between the orifice of the nozzle and the skin surface to be treated.

The dispensing system of the present invention can suitably be used to improve the appearance of skin by treating warts, moles, freckles, skin tags, age spots, lentigines, or other skin-related abnormalities. Accordingly, the invention also relates to a cosmetic method of treating skin, said method comprising topical application of a cryogenic dispersion onto the skin of a person or animal using the aforementioned dispensing system.

BACKGROUND OF THE INVENTION

Skin treatments to improve the appearance of skin are widely applied. Skin conditions often targeted by such treatments include warts, moles, freckles, skin tags, age spots (also known as liver spots), lentigines, or other skin-related abnormalities.

There are several types of procedures available that treat these skin conditions, ranging from topical ameliorations to more aggressive treatments such as laser treatment or cryogenic treatment. Topical treatments include lotions, creams, acids, bleaching agents and vitamins. However, such treatments typically are slow, result in subtle improvement of the skin, may cause hypo- or hyper-pigmentation, and are often insufficient.

To provide a more complete treatment of the skin, it is known to use laser therapy. Laser treatment, however, can cause unnecessary pain and extensive scarring.

Cryogenic treatments are also known in the art, and such treatments generally involve direct application of liquid nitrogen or another cryogen to a portion of the skin. The procedure is used often because of its efficacy and limited side effects.

When using cryogenic treatment, it is important to cool the treatment region to the proper temperature for an appropriate time. Cooling the region to too low a temperature can cause excessive damage. Cooling the region for too long a period of time can cause conduction of the cold temperature to neighboring tissue, increasing the size of the affected area. In addition, while surrounding tissue can survive a brief exposure to the very cold temperatures, prolonged exposure can cause tissue necrosis or excessive damage.

U.S. Pat. No. 5,516,505 describes a method of cryogenically treating a lesion on the surface of skin comprising the steps of:
- releasing a cryogenic agent from an aerosol or pressurized container in a manner such that the cryogenic agent accumulates into a synthetic plastic foam applicator,
- contacting the skin surface of a lesion with the synthetic plastic foam applicator having the accumulated cryogenic agent for a period of time sufficient to freeze the skin tissue such that permanent, irreversible rupture of cellular membranes of cells of the skin lesion occurs while the cryogenic agent is evaporating,
- subsequently removing the synthetic plastic foam applicator from the skin surface, and
- thereafter permitting the frozen skin tissue of the skin lesion to slowly thaw.

U.S. Pat. No. 5,125,546 describes an aerosol discharge valve assembly for regulating the flow of a liquid product from an aerosol container pressurized substantially by a permanent propellant gas, said assembly comprising:
- (a) a control valve mounted to said container;
- (b) an exit nozzle;
- (c) a tubular member projecting upwardly and outwardly of the container and defining a passage surmounted by said exit nozzle through which an atomized mixture of said propellant gas and liquid product can flow out of the container;
- (d) a tubular member projecting downwardly in said container, said control valve being operable between open and closed positions for controlling flow through said control valve and through said tubular members;
- (e) first passage means for conveying the liquid into said downwardly projecting tubular member under gas pressure for conveyance to a mixing region in said valve assembly; second passage means downstream of the first passage means for conveying the pressurized gas separately from the liquid product to said downwardly projecting tubular member for conveyance into said mixing region;
- (g) at least one intermediate choke restrictor between the mixing region and the exit nozzle through which the mixture of liquid product and pressurized gas is forced to pass; and
- (h) the size of the choke restrictor relative to said first and second passage means being selected to provide at least substantially sonic velocity choked flow through the choke restrictor at and above a selected minimum internal gas pressure, said mixed liquid product and propellant gas passing through said choke restrictor such that the liquid product, in response to changes from subsonic velocity flow to sonic velocity flow and the return to subsonic velocity flow, breaks up into fine liquid droplets comprising a highly dispersed foamed liquid product.

US 2004/102768 describes a cryotherapy apparatus adapted to be manipulated with one hand, using the expansion temperature and pressure of a liquefied gas sprayed in at least partially solid phase on a human or animal epidermis, contained under pressure in a removable cartridge, wherein the support of the cartridge and the controlled ejection and expansion system are disposed substantially in line and in the axis of the apparatus, inside an ergonomic housing whose axis corresponds to that of the apparatus, of which the median part serves as handle to be grasped by the adult user's hand and comprises the member for controlling the controlled gas ejection and expansion system of which the upper part presents an inlet for introducing into its support the cartridge, head down and in the axis of the housing, and for striking it or for withdrawing it after use, and of which the lower part comprises a calibrated opening forming a passage for the sprayed gas substantially in the axis of the housing and means for holding the outlet nozzle of the controlled ejection and expansion system at the required distance with respect to the zone of the epidermis to be treated.

WO 2016/010428 describes a nebulizer for the topical application of a liquid and/or solid to a surface, comprising:
a container designed for holding a colloidal substance and a medium;
an actuatable valve attached to the container; and
a nozzle attached to the valve, designed for generating a stream or spray,
wherein the valve:
comprises a mixing chamber attached to the nozzle; and
comprises a first and a second inlet attached to the mixing chamber for the separate delivery of the colloidal substance and the medium to the mixing chamber, wherein the mixing chamber is designed for forming a colloidal mixture comprising the colloidal substance and the medium before delivering the colloidal mixture to the nozzle, characterized in that the colloidal mixture comprises a dispersed phase consisting of a liquid and/or a solid substance and a continuous phase consisting of a propellant gas.

SUMMARY OF THE INVENTION

The inventors have developed a dispensing system for use in cryogenic skin treatment that is capable of targeted delivery of a cryogen at a high rate, thereby achieving rapid freezing of targeted skin tissue. The dispensing system of the present invention uses a cryogen that contains dimethyl ether and is designed to deliver the cryogen in an accurate and very effective manner.

The dispensing device of the present invention comprises:
a container comprising a liquid phase in direct contact and in equilibrium with a gas phase at a pressure of 2.5-8 bar, said liquid phase comprising liquefied dimethyl ether;
an actuatable valve attached to the container, said valve comprising:
  a mixing chamber comprising an inlet and an outlet, wherein the inlet comprises a Venturi tube having an entry cone for receiving gas phase from the container, an exit cone and a constricted section that connects the entry cone with the exit cone, said restricted section or said exit cone comprising a liquid inlet for receiving liquid phase from the container;
  a nozzle connected to the outlet of the mixing chamber;
a spacer attached to the container or to the valve, said spacer being adapted for defining a predetermined distance between the orifice of the nozzle and a skin surface to be treated; the distal end of the spacer being provided with a spray opening;
wherein the dispensing system is arranged to be used in a top-down position with the distal end of the spacer being in placed in direct contact with a skin surface to be treated and the nozzle being located below the container; and wherein, upon actuation of the valve during such top-down use:
the gas phase enters the mixing chamber through the Venturi tube thereby creating a Venturi effect that (i) draws the liquid phase into the exit cone of the Venturi tube via the liquid inlet and (ii) causes dispersal of the liquid phase into the gas phase; and
the resulting cryogenic liquid-in-gas dispersion is expelled through the orifice of the nozzle and through the spray opening of the spacer to deliver the cryogenic dispersion to the skin surface.

The dispensing device of the present invention is designed to provide very accurate delivery of the cryogenic dispersion at a high rate. Thus, the dispensing device can be used to effectively treat skin abnormalities with minimal damage to surrounding skin tissue.

The invention also provides a cosmetic method of treating skin, said method comprising topical application of a cryogenic dispersion onto the skin of a person or animal using the aforementioned dispensing system.

DETAILED DESCRIPTION OF THE INVENTION

Accordingly, a first aspect of the invention relates to dispensing system for use in cryogenic skin treatment, said system comprising:
a container having an internal volume of 10-200 ml, said container comprising a liquid phase in direct contact and in equilibrium with a gas phase at a pressure of 2.5-8 bar, said liquid phase comprising at least 50 wt. % liquefied dimethyl ether;
an actuatable valve attached to the container, said valve comprising
  a mixing chamber having an operational internal volume of 10-600 µl and comprising an inlet and an outlet, wherein the inlet comprises a Venturi tube having an entry cone for receiving gas phase from the container, an exit cone and a constricted section that connects the entry cone with the exit cone, said constricted section or said exit cone comprising a liquid inlet for receiving liquid phase from the container, the liquid inlet having a cross-sectional opening area of $8 \times 10^{-3}$ to $100 \times 10^{-3}$ mm$^2$ and the constricted section having a cross-sectional opening area that is at least 150% larger than the cross-sectional opening area of the liquid inlet;
  a nozzle connected to the outlet of the mixing chamber, said nozzle comprising an orifice with a cross-sectional opening area in the range of $8 \times 10^{-3}$ to $100 \times 10^{-3}$ mm$^2$;
a spacer attached to container or to the valve, said spacer being adapted for defining a predetermined distance between the orifice of the nozzle and a skin surface to be treated; the distal end of the spacer being provided with a spray opening, the distance between said spray opening and the orifice of the nozzle being in the range of 2 to 25 mm;
wherein the dispensing system is arranged to be used in a top-down position with the distal end of the spacer being in placed in direct contact with skin around a skin surface to be treated and the nozzle being located below the container; and wherein, upon actuation of the valve during such top-down use:
the gas phase enters the mixing chamber through the Venturi tube thereby creating a Venturi effect that (i) draws the liquid phase into the Venturi tube via the liquid inlet and (ii) causes dispersal of the liquid phase into the gas phase; and
the resulting cryogenic liquid-in-gas dispersion is expelled through the orifice of the nozzle and through the spray opening of the spacer to deliver the cryogenic dispersion to the skin surface to be treated at a rate of 30-200 mg/s.

The dispensing system of the present invention is arranged to be used in a top-down position in which the nozzle is located below the container. In this top-down position the bulk of the liquid phase in the container is located above the nozzle.

The term "cross-sectional opening area" as used herein refers to the minimum cross-sectional area of an aperture or of a conduit, normal to the main flow through said aperture or conduit. In case of a spherical opening, the cross-sectional opening area equals $\pi r^2$, wherein r is the radius of the spherical opening.

The present invention encompasses embodiments of the dispensing system in which the volume of the mixing chamber changes upon actuation of the actuatable valve. The term "operational volume" refers to the volume of the mixing chamber upon full actuation of the valve.

The pressure at which the liquid phase and the gas phase are contained in the container is determined at 20° C.

The rate at which the cryogenic dispersion is delivered to the skin surface by the present dispensing device is determined at 20° C. and atmospheric pressure.

The requirement that the constricted section has a cross-sectional opening area that is at least 150% larger than the cross-sectional opening area of the liquid inlet means that if the liquid inlet has a cross-sectional opening area of 0.12 $mm^2$, the constricted section has to have a cross-sectional opening area of at least 0.3 $mm^2$.

The container typically has an internal volume of 20-150 ml, more particularly of 25-120 ml. The liquid phase and gas phase are preferably present in the container at a pressure of 3-7 bar.

The entry cone of the Venturi tube is preferably connected to a drawing tube that extends into the container. A largest diameter of the entry cone preferably is at least 0.6 mm, more preferably in the range of 0.6 to 3 mm. The drawing tube typically does not extend until near the distal end of the container. More particularly, it is preferred that during the complete use cycle of the dispensing system the drawing tube does not extend into the liquid phase within the container when the dispensing system is in a top-up position with the nozzle being located above the container. Thus, no cryogenic dispersion is released from the dispensing system when the valve is actuated in the top-up position. When the valve is actuated in the top-down position, however, the gas phase enters the mixing chamber through the Venturi tube and the resulting Venturi effect can draw up the liquid phase through the liquid inlet into the Venturi tube if there still is sufficient liquid phase present in the container to feed into the liquid inlet. The Venturi effect also causes dispersal of the liquid phase into the gas phase under the formation of the cryogenic dispersion.

The cross-sectional opening area of the drawing tube preferably is at least 70% larger, more preferably at least 130% larger than the cross-sectional opening area of the constricted section of the Venturi tube.

In accordance with another preferred embodiment, the liquid inlet of the Venturi tube connects the constricted section or the exit cone of the Venturi tube with the interior of the container adjacent to the valve.

The liquid inlet is preferably located in the exit cone of the Venturi tube.

The constricted section of the Venturi tube typically has a cross-sectional opening area of 0.12-0.50 $mm^2$, more preferably of 0.16-0.44 $mm^2$ and most preferably of 0.20-0.38 $mm^2$.

The Venturi tube preferably has an entry cone of 30-90 degrees, more preferably of 35-80 degrees and most preferably 40-70 degrees.

The Venturi tube preferably has an exit cone of 10-40 degrees, more preferably of 15-35 degrees and most preferably 20-32 degrees.

According to a particularly preferred embodiment, the entry cone has a cone angle that is at least 30%, preferably at least 50% and most preferably at least 70% larger than the cone angle of the exit cone. In case of an exit cone of 28 degrees, the requirement that the entry cone is at least 70% larger means that the entry cone should be at least 47.6 degrees.

The liquid inlet preferably has a cross-sectional opening area of $18\times10^{-3}$ to $72\times10^{-3}$ $mm^2$, more preferably of $25\times10^{-3}$ to $62\times10^{-3}$ $mm^2$.

The constricted section of the Venturi tube preferably has a cross-sectional opening area that is at least 200%, more preferably 300-800% larger than the cross-sectional opening area of the liquid inlet.

The mixing chamber preferably has an operational internal volume of 20-500 more preferably of 40-400 μl.

The nozzle orifice preferably has a cross-sectional opening area in the range of $11\times10^{-3}$ to $72\times10^{-3}$ $mm^2$, more preferably in the range of $13\times10^{-3}$ to $50\times10^{-3}$ $mm^2$ and most preferably in the range of $15\times10^{-3}$ to $35\times10^{-3}$ $mm^2$.

The cryogenic dispersion is typically expelled through the orifice of the nozzle forming a spray cone with an angle of not more than 40 degrees, more preferably of not more than 30 degrees and most preferably of not more than 20 degrees.

Besides dimethyl ether the liquid phase may contain other components such as propellants other than dimethyl ether, keratolytics (e.g. glycolic acid or salicylic acid), emollients, anti-oxidants, trichloroacetic acid, dichloroacetic acid, monochloroacetic acid, and co-solvents.

In one embodiment of the invention the liquid phase contains at least 90 wt. % dimethyl ether. More preferably, the liquid phase consists of dimethyl ether and is in equilibrium with a gas phase that also consists of dimethyl ether.

In another embodiment, the liquid phase contains at least 90 wt. %, more preferably at least 95 wt. % of a mixture of dimethyl ether and one or more alkanes selected from propane, n-butane and isobutane. More preferably, the liquid phase and the gas phase consist of a mixture of dimethyl ether and said one or more alkanes.

The liquid phase preferably contains at least 90 wt. %, more preferably at least 95 wt. % of a mixture of dimethyl ether and propane. More preferably, the liquid phase and the gas phase consist of a mixture of dimethyl ether and propane.

According to a particularly preferred embodiment, the mixture of dimethyl ether and the one or more alkanes contains dimethyl ether and the one or more alkanes in a weight ratio of 1:1 to 9:1, more preferably of 3:2 to 5:1 and most preferably of 2:1 to 4:1.

Preferably, the distance between orifice of the nozzle and the spray opening of the spacer is in the range of 4 to 22 mm, more preferably in the range of 8 to 20 mm, most preferably in the range of 10 to 18 mm.

The spray opening of the spacer preferably has a minimum diameter of 2-10 mm, more preferably of 3-9 mm and most preferably of 4-8 mm.

The minimum and maximum diameter of spray opening of the spacer are preferably of the same order of magnitude. Typically, the spray opening has an aspect ratio of less than 2:1, more preferably of less than 1.5:1, most preferably of less than 1.2:1.

The spacer preferably comprises a solid element defining an internal chamber that forms a spray conduit and that has the spray opening at its distal end.

The solid element of the spacer preferably comprises at least one opening. The at least one opening facilitates evaporation of the cryogenic suspension once it has been sprayed onto the skin surface. In addition, the at least one opening allows the user to verify that the cryogenic dispersion is adequately delivered to the skin surface.

The dispensing system preferably is arranged in such a way that the distance between the spray opening and the nozzle orifice does not change upon actuation of the valve. This may advantageously be realised by attaching the spacer to the valve.

In a particularly preferred embodiment, the actuatable valve comprises a fixed part fixed to the container and comprising the Venturi tube and the liquid inlet and forming a circumferential sidewall of the mixing chamber, the valve further comprising a moveable part that is moveable with respect to the fixed part between a valve-open position and a valve-closed position, said moveable part comprising the nozzle, wherein the nozzle has a circumferential side wall surrounding a channel for the liquid-in-gas dispersion and a through opening in said side wall, wherein the through opening is arranged such that in the valve-open position the through opening fluidly connects the mixing chamber and the orifice of the nozzle, and in the valve-closed position the moveable part and fixed part together seal off a passage between the mixing chamber and the through opening. According to an even more preferred embodiment, the fixed part is provided with a gasket through which the moveable part extends, wherein when the moveable part is in the valve-closed position the gasket seals off the passage between the mixing chamber and the through opening.

In yet another preferred embodiment of the present dispensing system, at an end opposite from the nozzle the container has a top wall, the system further comprising a holder for moveably holding the container therein, wherein the spacer and the nozzle are fixed with respect to the holder and the holder surrounds a substantial portion of a circumferential outer wall of the container while leaving the top wall at least partially free for allowing the valve to be actuated by a user by pressing his or her finger on the top wall of the container relative to the holder towards the spray opening. This embodiment offers the advantage that the dispensing system can be operated single handedly.

The spray opening in the spacer preferably extends through a contact surface of the spacer that is adapted for making contact with skin surrounding the skin to be treated, wherein said contact surface extends substantially normal to the spray direction of the orifice of the nozzle.

The spray opening is preferably surrounded by cover means comprising an edge, preferably a circumferential edge, which prevents application of cryogenic dispersion onto skin other than through the spray opening.

Upon actuation of the valve, the cryogenic dispersion is preferably delivered to the skin surface at a rate of 35-120 mg/s, most preferably of 40-100 mg/s.

An alternative embodiment of the present invention relates to dispensing device as described herein before, except that 1,1,1,2-tetrafluoroethane is used instead of dimethyl ether. In other words, in accordance with this embodiment, the liquid phase in the container contains 1,1,1,2-tetrafluoroethane.

Preferably, in accordance with this alternative embodiment, the liquid phase contains at least 50 wt. %, more preferably at least 80 wt. % and most preferably at least 1,1,1,2-tetrafluoroethane.

Yet another alternative embodiment of the present invention relates to dispensing device as described herein before, except that 2,3,3,3-tetrafluoropropene is used instead of dimethyl ether. In other words, in accordance with this embodiment, the liquid phase in the container (contains 2,3,3,3-tetrafluoropropene.

Preferably, in accordance with this alternative embodiment, the liquid phase contains at least 50 wt. %, more preferably at least 80 wt. % and most preferably at least 2,3,3,3-tetrafluoropropene.

Another aspect of the invention relates to a cosmetic method of treating skin, said method comprising topical application of a cryogenic dispersion onto the skin of a person or animal using a dispensing system as described herein.

According to a preferred embodiment of the present method the cryogenic dispersion is applied to a wart, a mole, a freckle, a skin tag, an age spot or a lentigine. Most preferably, the cryogenic dispersion is applied to a wart.

Typically, the cryogenic dispersion is continuously delivered to the skin using the dispensing system during a period of 2 to 30 seconds, more preferably of 4-20 seconds.

BRIEF DESCRIPTION OF THE DRAWINGS

Below the present invention is further explained with reference to the drawings, in which FIGS. 1A, 1B, 1C, 1D, 1E: schematically show cross-sectional representations of a dispensing system, and details thereof, according to the present invention;

FIGS. 2A, 2B, 2C: show representations of a dispensing system according to the present invention, provided with a holder around the container FIGS. 1A and 1B respectively show a dispensing system 1 according to the present invention, with an actuatable valve 20 closed so that fluid and gas from within the interior of the container are blocked from exiting the container through nozzle 30, and with the valve 20 open so that the nozzle is in fluid communication with the interior of the container 10. Though in the embodiments shown the nozzle comprises two parts, 32, 33 which are attached to each other, it will be appreciated that the nozzle may instead be formed as a single unit.

The container has an internal volume of about 120 ml, for containing a liquid phase 11 and a gas phase 12 which are in direct contact with each other. In the embodiment shown, the liquid phase and gas phase are both at a pressure of around 4bar, and the liquid phase 11 consists of liquefied dimethyl ether. Alternatively, the liquid phase 11 may consist of a 3:1. (w/w) mixture liquefied dimethyl ether and liquefied propane.

The nozzle 30 of the valve 20 is attached to the container 10. A spacer 40 is fixed to the container and ensures that orifice 31 of the nozzle 30 remains spaced apart from spray opening 41 of the spacer 40. The orifice of the nozzle has a relatively small cross-sectional opening area in the range of 0.018-0.07 $mm^2$ through which a directed spray of liquid-in-gas dispersion 50 can be ejected towards the opening 41 of the spacer, which opening 41 has a larger cross-sectional opening area in a plane normal to the longitudinal direction of the nozzle. During use, e.g. when cryogenically treating a wart, the dispensing system is positioned such that a contact surface 48 of the spacer makes contact with the skin surrounding the skin area to be treated and such that the skin to be treated 80 is accessible through the opening 41. A view-port 46 in the sidewall 47 of the spacer allows a view of the skin to be treated from a side of the spacer facing away from the contact surface 48, thus facilitating positioning of the dispensing device as well as inspection of the skin during treatment. The view port preferably comprises an opening in the sidewall 47, so that condensation from the liquid-in-gas dispersion can leave the spacer without having to remove the spacer from the skin and without blocking view of the skin to be treated.

Figure 1B:
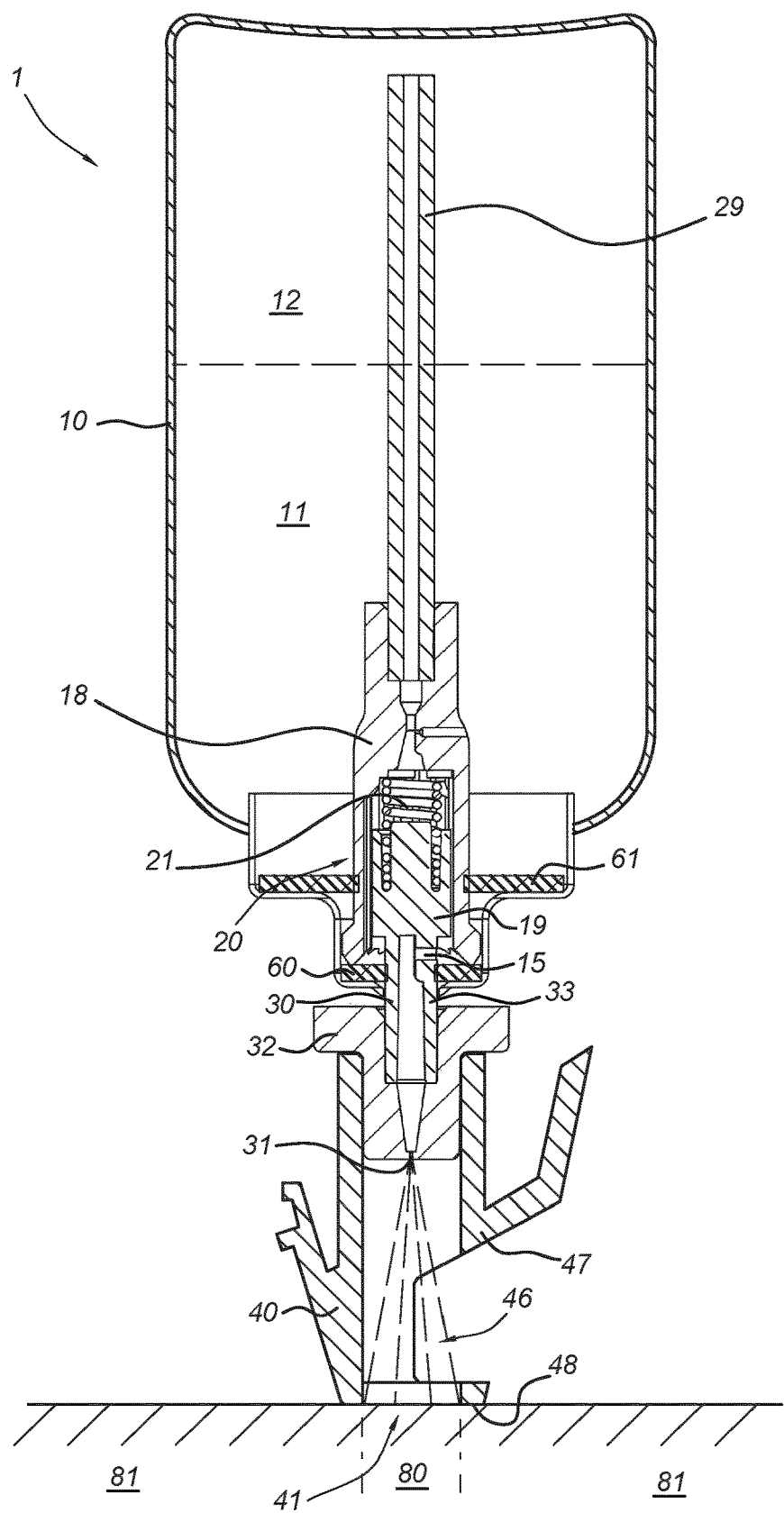
Figure 1C:
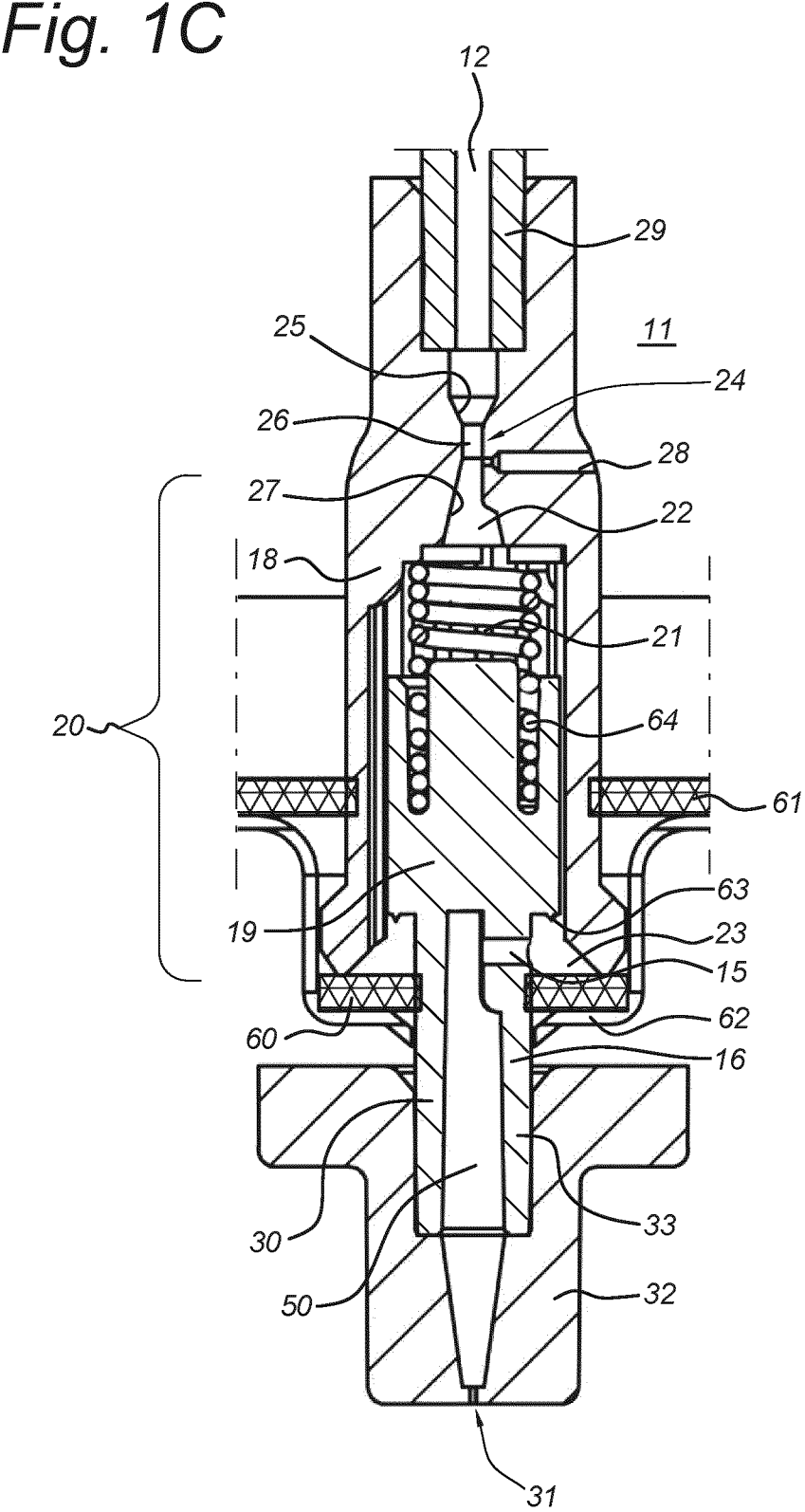

The valve 20 comprises a fixed part 18 that is fixed to the container 10, and a moveable part 19 which is moveable relative to the container between a valve-closed position, shown in FIG. 1A, and a valve-open position, shown in FIG. 1B. FIG. 1C shows the valve of 20 in greater detail, in the valve open position, however with the space 40 not shown for reasons of clarity. The moveable part 19 and the fixed part 18 together form a mixing chamber 21 with an inlet 22 for supply of liquid phase 11 and phase 12 to the mixing chamber. The volume of the mixing chamber depends on the position of the moveable part 19 relative to the fixed part, and has a volume of about 200 µl when the upon full actuation of the valve to the valve-open position. For receiving gas phase 12 from the container, the inlet is provided with a Venturi tube 24 having an entry cone 25 that in turn is connected to a drawing tube 29 that extends into the container. The Venturi tube tapers towards a constricted section 26 to which it is connected, which section 26 in turn is connected to an exit cone 27 that debauches in the mixing chamber 21. The constricted section 26 further comprises a liquid inlet 28 for receiving liquid phase 11 from the container 10. When the device is in the top-down position and the moveable part 19 is moved in the valve-open position, as shown in FIGS. 1B and 1C, the propellant gas 12 flows through the Venturi tube 24, causing underpressure in the liquid inlet 28, as a result of which liquid 11 is drawn into the mixing chamber 21 together with the propellant gas 12, where the two phases are further mixed to form a liquid-in-gas dispersal. Also with reference to FIG. 1B, the liquid-in-gas dispersal 50 is ejected out of the mixing chamber 21, through a through-opening 15 in side wall 16 of the nozzle 30, and out of nozzle orifice 31 to the spray opening 41. The moveable part 19 can be held in the valve-open position for any desired amount of time, e.g. until the pressure within the container is substantially equal to the pressure outside of the dispenser system.

Figure 1D:
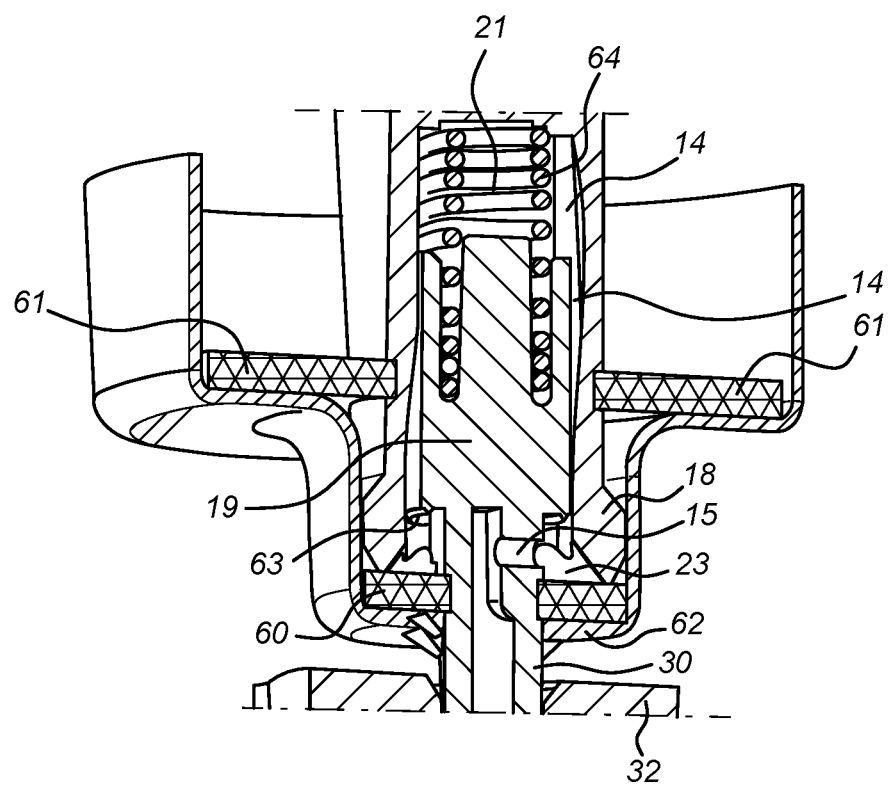

FIG. 1D schematically shows a cross-section isometric view of a portion of the dispensing system, with the moveable part 19 is in in the valve open position, which illustrates how liquid-in-gas dispersal can travel from the mixing chamber 21 along recessed portions 14 on the inner circumference of the fixed part 18 to the outlet 23 of the mixing chamber.

Referring to FIG. 1D as well as to FIG. 1A, when the moveable part 19 is in the valve-closed position, the fluid communication between the mixing chamber 21 and the interior of the container 10 where the gas phase 12 and liquid phase 11 are contained remains open. However, fluid communication from the mixing chamber 21 to the nozzle 30 via through opening 15 is sealed off by gasket 60 through which the nozzle 30 extends, and which gasket sealingly abuts a shoulder 63 of the fixed part 18 that is urged against the gasket by spring 64. The gasket 60 is thus compressed between the shoulder 63 of the moveable part 19 and the bottom wall 62 of the container 10. An additional gasket 61 is attached to the moveable part 19 for preventing gas and/or liquid from escaping from the container 10 along the outer surface of the moveable part.

Figure 1E:
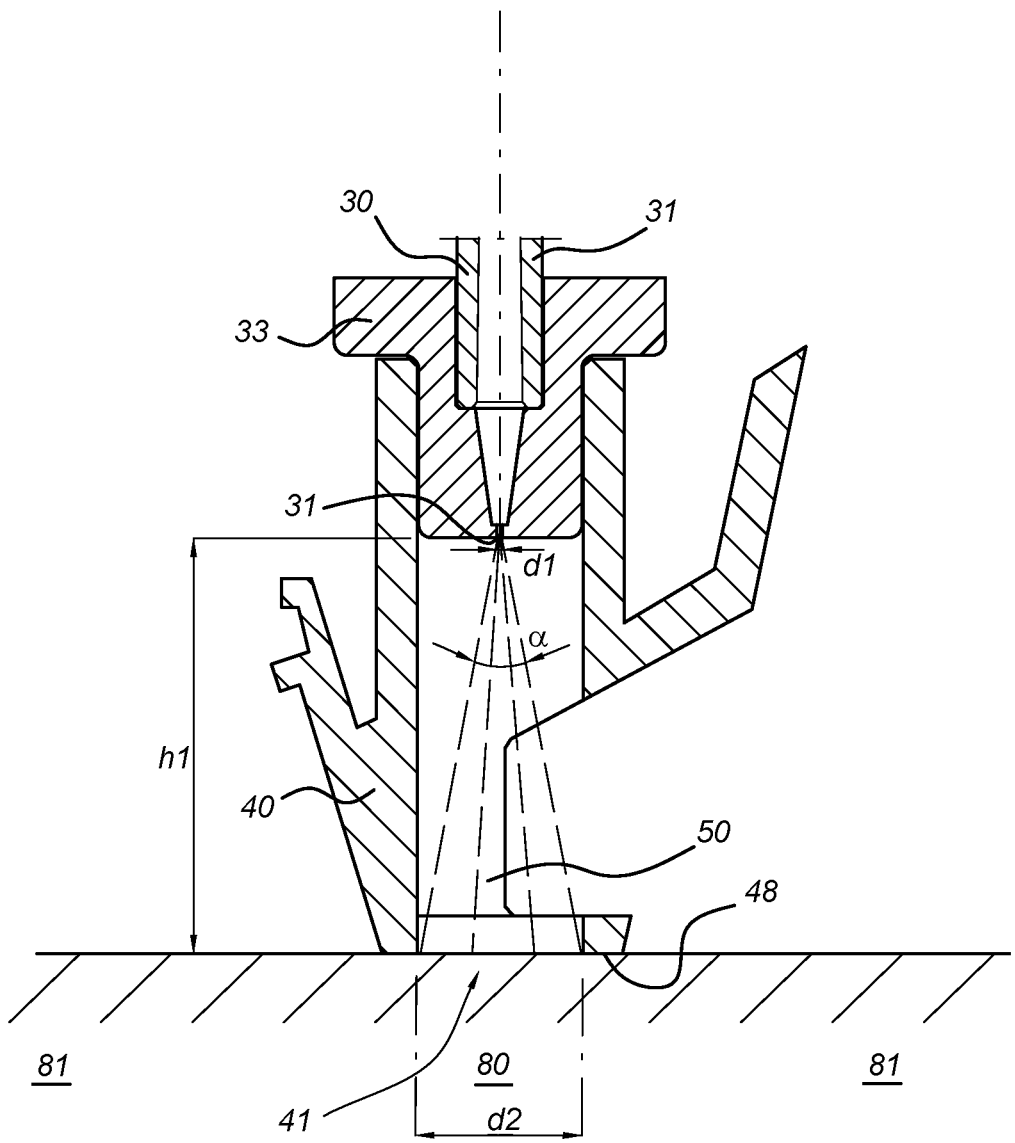

FIG. 1E shows a detail of a portion of the nozzle 30 and the spacer 40. The nozzle orifice 31 has a relatively small diameter d1 of between 0.15-0.30 mm to ensure that the liquid-in-gas dispersal 50 is ejected from the orifice in a narrow spray cone. The angle α of the spray cone is about 30 degrees. The contacting surface 48 of the spacer 40 is in contact with a skin portion 80 while leaving skin to be treated free. The liquid-in gas dispersal 50 can thus reach the portion of skin to be treated that lies under the spray opening 41. The spray opening 41 lies at a fixed distance h1 of between 2 and 25 mm from the orifice 31, independent of whether the valve is in the valve-open or in the valve-closed position.

Figure 2A:
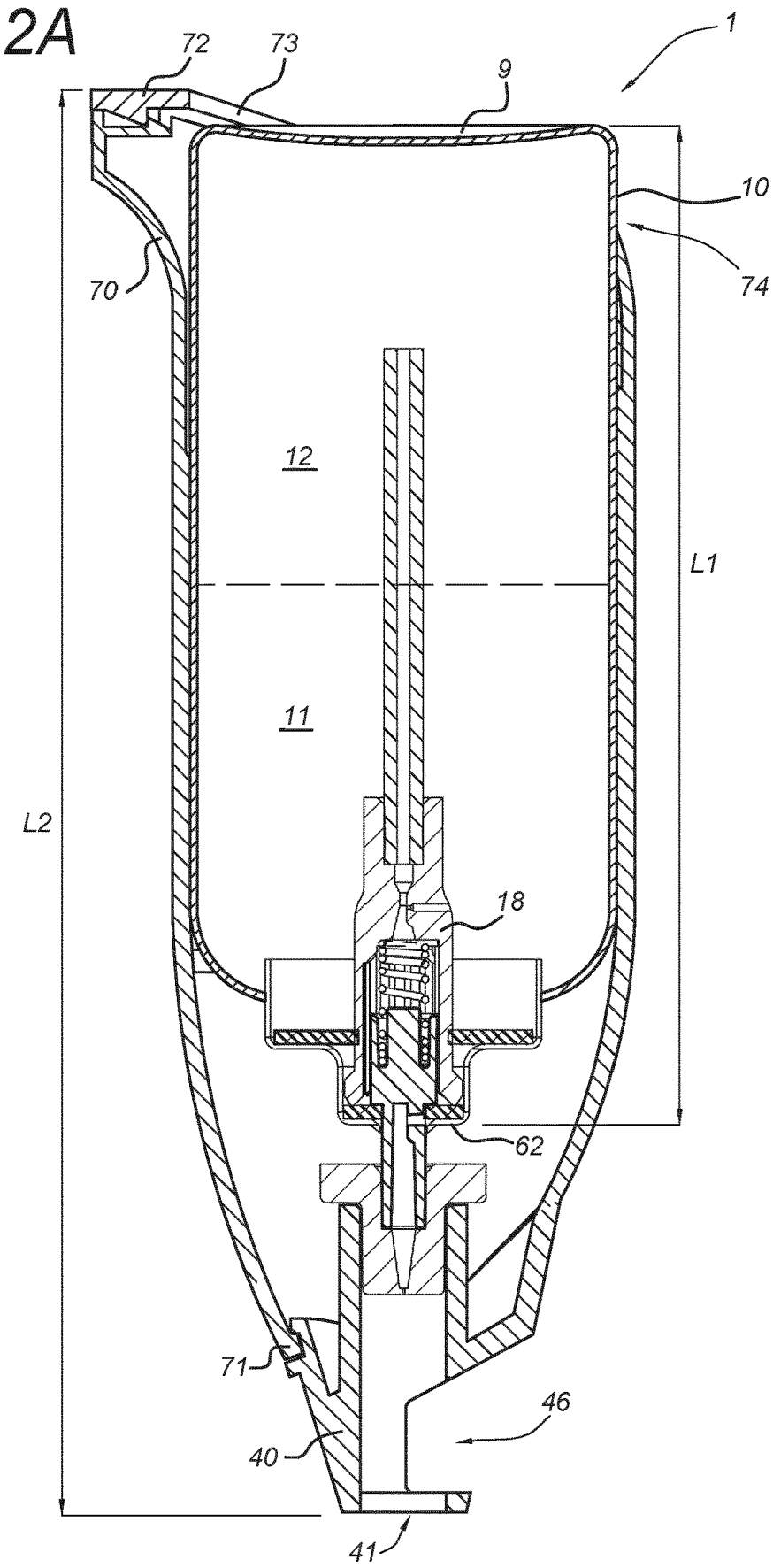
Figure 2B:
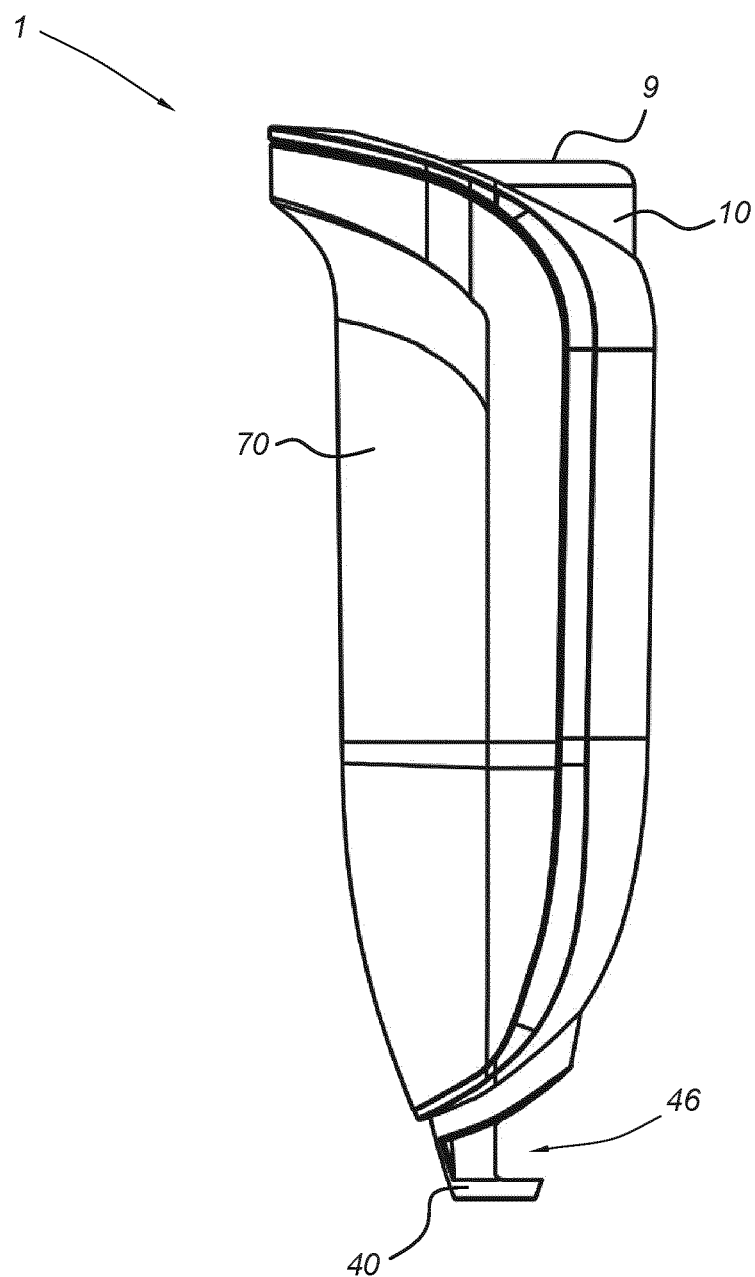
Figure 2C:
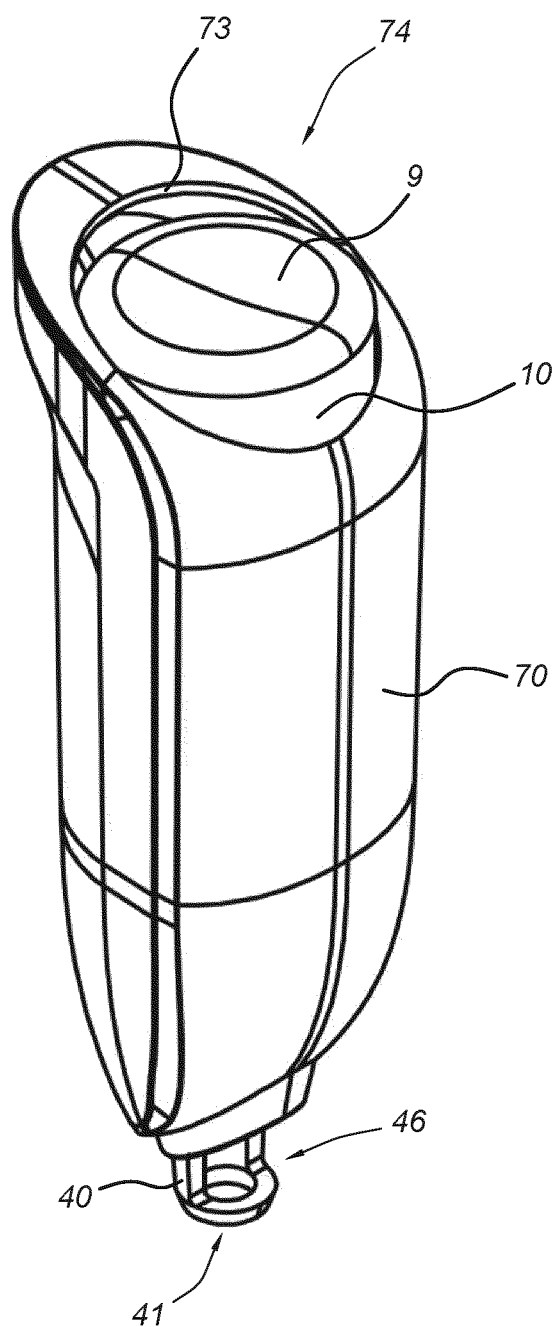

FIGS. 2A, 2B and 2C respectively show a schematical cross-sectional side view, a side view and an isometric view of the dispensing system according to the present invention, further comprising a holder 70 for holding the container therein in such a manner that the container 10 can be moved relative to the holder along the longitudinal direction L of both. Though the container 10 typically comprises a metal, the holder may be made from a plastics material that is more flexible than the container. During use, position of the holder 70 relative to the nozzle 30 and the spacer 40 is fixed, regardless of whether the valve is open or closed. The spacer 40 is attached to holder at a bottom side 71 of the holder 70, while at its opposite topside 72 the holder leaves free a portion of the top wall 9 of container 10 which lies opposite to the bottom wall 62 of the container. When the spacer 40 is in contact with skin to be treated, a user can press the top wall 9 of the container 10 downwards relative to the holder and towards spray-opening 41, e.g. by pushing his finger or thumb against the top wall 9, in this manner also moving the moveable part 19 of the actuator valve 20 to the valve-open position.

As can be seen more clearly in FIG. 2A, the length L1 of the container 10 is smaller than the length L2 of the holder 70 and space 40 combined. More in particular, the holder extends over a length greater than the length of the container held therein. Near its top side 72, the holder is provided with an opening 74 through which the container 10 can be inserted into and taken out of from the holder 70. The opening has an edge 73 which, when projected onto the top wall 9 of the container in a plane normal to the longitudinal direction of the container, overlaps a portion of the top wall 9 of the container 10. The edge 73 thus helps prevent the container from accidentally falling out of the holder 70. When the gas phase and/or liquid phase in the container has been used up, the container can be taken out of the holder to be replaced with another container.

What is claimed is:

1. A dispensing system for use in cryogenic skin treatment, the system comprising:
(a) a container having an internal volume of 10-200 ml and comprising a liquid phase in direct contact and in equilibrium with a gas phase at a pressure of 2.5-8 bar, the liquid phase comprising at least 50 wt. % liquefied dimethyl ether;
(b) an actuatable valve attached to the container, the valve comprising:
(i) a mixing chamber having an operational internal volume of 10-600 µl and comprising an inlet and an outlet, wherein the inlet comprises a Venturi tube having an entry cone for receiving the gas phase from the container, an exit cone, and a constricted section that connects the entry cone with the exit cone, the constricted section or the exit cone comprising a liquid inlet for receiving the liquid phase from the container, the liquid inlet having a cross-sectional opening area of $8\times10^{-3}$ to $100\times10^{-3}$ mm$^2$ and the constricted section having a cross-sectional opening area of 0.012 to not more than 0.5 mm$^2$ and at least 150% larger than the cross-sectional opening area of the liquid inlet;
  (ii) a nozzle connected to the outlet of the mixing chamber, the nozzle comprising an orifice with a cross-sectional opening area in the range of $8\times10^{-3}$ to $100\times10^{-3}$ mm$^2$;
(c) a spacer attached to the container or to the valve, the spacer being adapted for defining a predetermined distance between the orifice of the nozzle and a skin surface to be treated; the distal end of the spacer being provided with a spray opening, the distance (h1) between the spray opening and the orifice of the nozzle being in the range of 2 to 25 mm;
wherein the dispensing system is arranged to be used in a top-down position with the distal end of the spacer being placed in direct contact with skin around a skin surface to be treated and the nozzle being located below the container; and
wherein the apparatus is configured such that upon actuation of the valve during such top-down use, the gas phase enters the mixing chamber through the Venturi tube thereby creating a Venturi effect that
  (i) draws the liquid phase into the Venturi tube via the liquid inlet and
  (ii) causes dispersal of the liquid phase into the gas phase; and
the resulting cryogenic liquid-in-gas dispersion is expelled through the orifice of the nozzle and through the spray opening of the spacer to deliver the cryogenic dispersion to the skin surface to be treated at a rate of 30-200 mg/s.

2. The dispensing system according to claim 1, wherein the entry cone of the Venturi tube is connected to a drawing tube that extends into the container.

3. The dispensing system according to claim 1, wherein the liquid inlet of the Venturi tube connects the constricted section or the exit cone of the Venturi tube with the interior of the container adjacent to the valve.

4. The dispensing system according to claim 1, wherein the constricted section of the Venturi tube has a cross-sectional opening area of 0.12 to 0.5 mm$^2$.

5. The dispensing system according to claim 1, wherein the Venturi tube has an entry cone of 30-90 degrees.

6. The dispensing system according to claim 1, wherein the Venturi tube has an exit cone of 10-40 degrees.

7. The dispensing system according to claim 1, wherein the cryogenic dispersion is expelled through the orifice of the nozzle forming a spray cone with an angle of not more than 40 degrees.

8. The dispensing system according to claim 1, wherein the liquid phase comprises at least 90 wt. % dimethyl ether.

9. The dispensing system according to claim 1, wherein the liquid phase comprises at least 90 wt. % of a mixture of dimethyl ether and one or more alkanes selected from propane, n-butane and isobutane.

10. The dispensing system according to claim 1, wherein the spray opening of the spacer has a minimum diameter of 2-10 mm.

11. The dispensing system according to claim 1, wherein the actuatable valve comprises a fixed part fixed to the container and comprising the Venturi tube and the liquid inlet and forming a circumferential sidewall of the mixing chamber, the valve further comprising a moveable part that is moveable with respect to the fixed part between a valve-open position and a valve-closed position and comprises the nozzle,
  wherein the nozzle has a circumferential side wall surrounding a channel for the liquid-in-gas dispersion and a through opening in the side wall,
  wherein the through opening is arranged such that in the valve-open position the through opening fluidly connects the mixing chamber and the orifice of the nozzle, and in the valve-closed position the moveable part and fixed part together seal off a passage between the mixing chamber and the through opening.

12. The dispensing system according to claim 11, wherein the fixed part is provided with a gasket through which the moveable part extends, wherein when the moveable part is in the valve-closed position the gasket seals off the passage between the mixing chamber and the through opening.

13. The dispensing system according to claim 1, wherein at an end opposite from the nozzle the container has a top wall, the system further comprising a holder for moveably holding the container therein,
  wherein the spacer and the nozzle are fixed with respect to the holder and the holder surrounds a substantial portion of a circumferential outer wall of the container while leaving the top wall at least partially free for allowing the valve to be actuated by a user by pressing his or her finger on the top wall end of the container relative to the holder towards the spray opening.

14. A method of treating skin, the method comprising topically applying a cryogenic dispersion onto the skin of a person or animal using a dispensing system according to claim 1.

15. The method according to claim 14, wherein the cryogenic dispersion is applied to a wart, a mole, a freckle, a skin tag, an age spot or a lentigine.

* * * * *